United States Patent
Sauer

(10) Patent No.: US 9,943,303 B2
(45) Date of Patent: Apr. 17, 2018

(54) METHOD OF PASSING SUTURE TAILS THROUGH A SURGICAL PLEDGET

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

(*) Notice: Subject to any disclaimer, the term of this patent is extended or adjusted under 35 U.S.C. 154(b) by 872 days.

(21) Appl. No.: 14/309,972

(22) Filed: Jun. 20, 2014

(65) Prior Publication Data

US 2015/0366554 A1 Dec. 24, 2015

Related U.S. Application Data

(63) Continuation of application No. 13/100,606, filed on May 4, 2011, now Pat. No. 8,795,295.

(51) Int. Cl.
*A61B 17/04* (2006.01)

(52) U.S. Cl.
CPC ...... *A61B 17/0401* (2013.01); *A61B 17/0485* (2013.01); *A61B 17/0487* (2013.01); *A61B 2017/0406* (2013.01); *A61B 2017/0409* (2013.01)

(58) Field of Classification Search
CPC ............. A61B 17/0482; A61B 17/0485
See application file for complete search history.

(56) References Cited

U.S. PATENT DOCUMENTS

| | | |
|---|---|---|
| 4,823,794 A | 4/1989 | Pierce |
| 5,219,359 A | 6/1993 | McQuilkin |
| 5,520,702 A | 5/1996 | Sauer |
| 5,643,289 A | 7/1997 | Sauer |
| 5,669,917 A | 9/1997 | Sauer |
| 5,733,308 A | 3/1998 | Daugherty |
| 5,800,447 A | 9/1998 | Wenstrom |
| 6,171,317 B1 | 1/2001 | Jackson |
| 6,368,334 B1 | 4/2002 | Sauer |
| 6,506,197 B1 | 1/2003 | Rollero |
| 6,641,592 B1 | 11/2003 | Sauer |
| 6,997,931 B2 | 2/2006 | Sauer |
| 7,235,086 B2 | 6/2007 | Sauer |
| 7,731,727 B2 | 6/2010 | Sauer |
| 8,795,295 B2 | 8/2014 | Sauer |
| 2002/0068949 A1 | 6/2002 | Williamson |
| 2005/0261708 A1 | 11/2005 | Pasricha |

(Continued)

FOREIGN PATENT DOCUMENTS

WO WO2001/017446 3/2001

OTHER PUBLICATIONS

Sep. 26, 2012 International Search Report for PCT Application PCT/2012/036427.

*Primary Examiner* — Gregory Anderson
(74) *Attorney, Agent, or Firm* — Christopher B. Miller

(57) ABSTRACT

A method of passing suture through a pledget is disclosed. A first suture tail is passed through a first suture engaging loop extending out of a first aperture in the pledget on a distal side of the pledget. A second suture tail is passed through a second suture engaging loop extending out of a second aperture in the pledget on the distal side of the pledget. The first and second suture tails are drawn proximally through their respective pledget apertures by pulling a handle coupled to the first and second suture engaging loops on a proximal side of the pledget.

20 Claims, 7 Drawing Sheets

(56) References Cited

U.S. PATENT DOCUMENTS

2010/0010497 A1   1/2010  Goble
2010/0256677 A1  10/2010  Albertorio
2012/0016383 A1   1/2012  Sauer
2012/0283749 A1* 11/2012  Sauer ................. A61B 17/0401
                                                  606/144

* cited by examiner

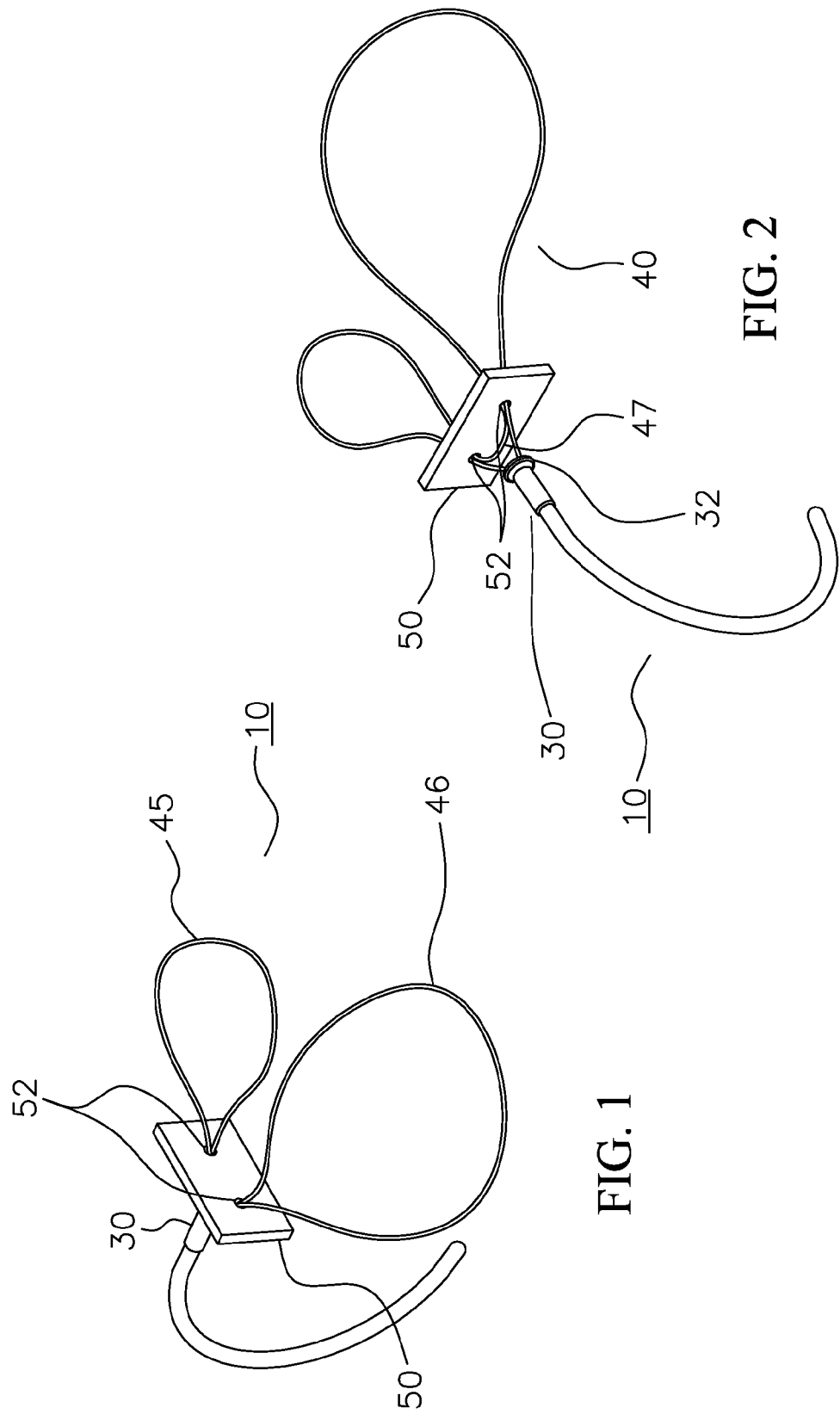

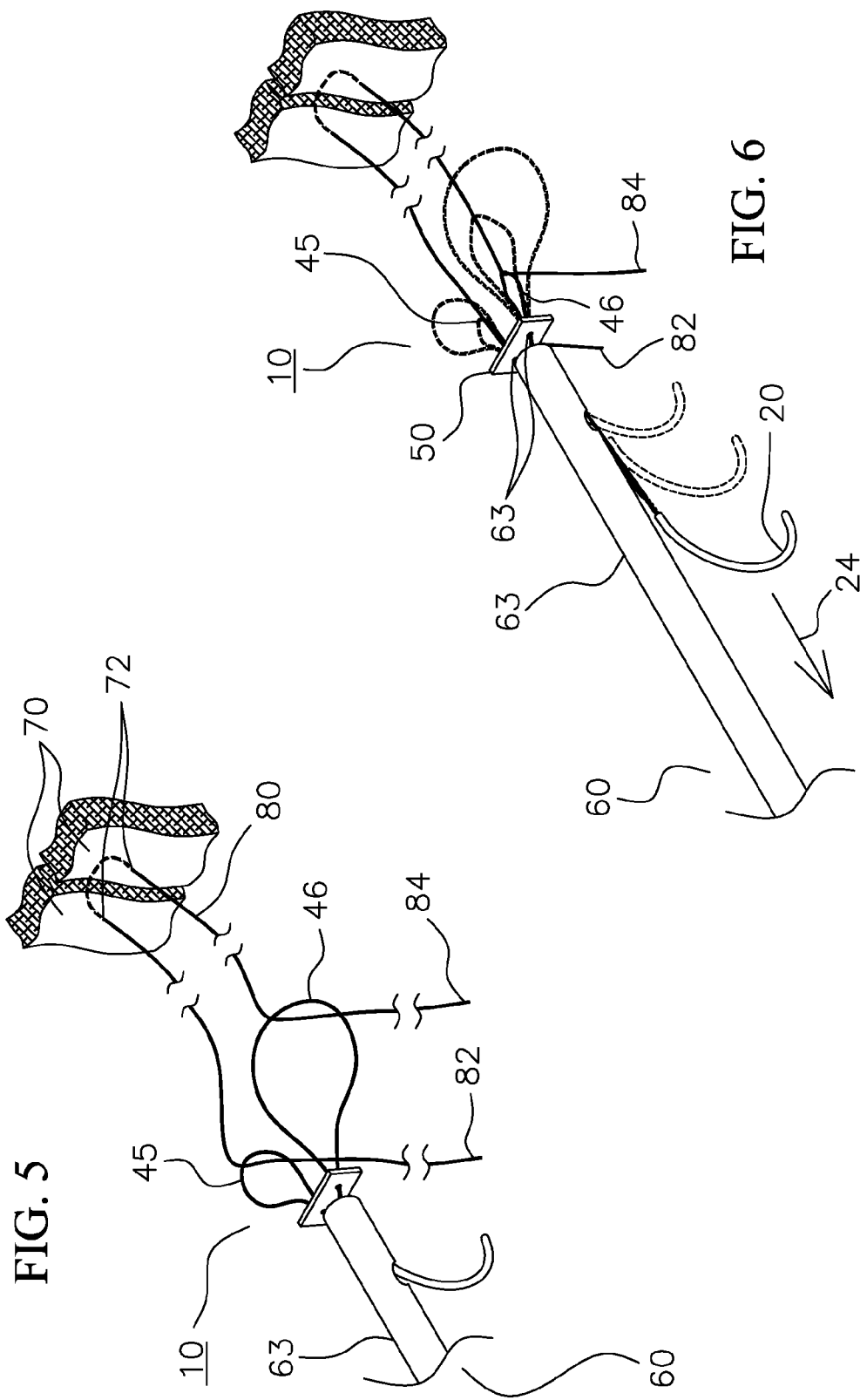

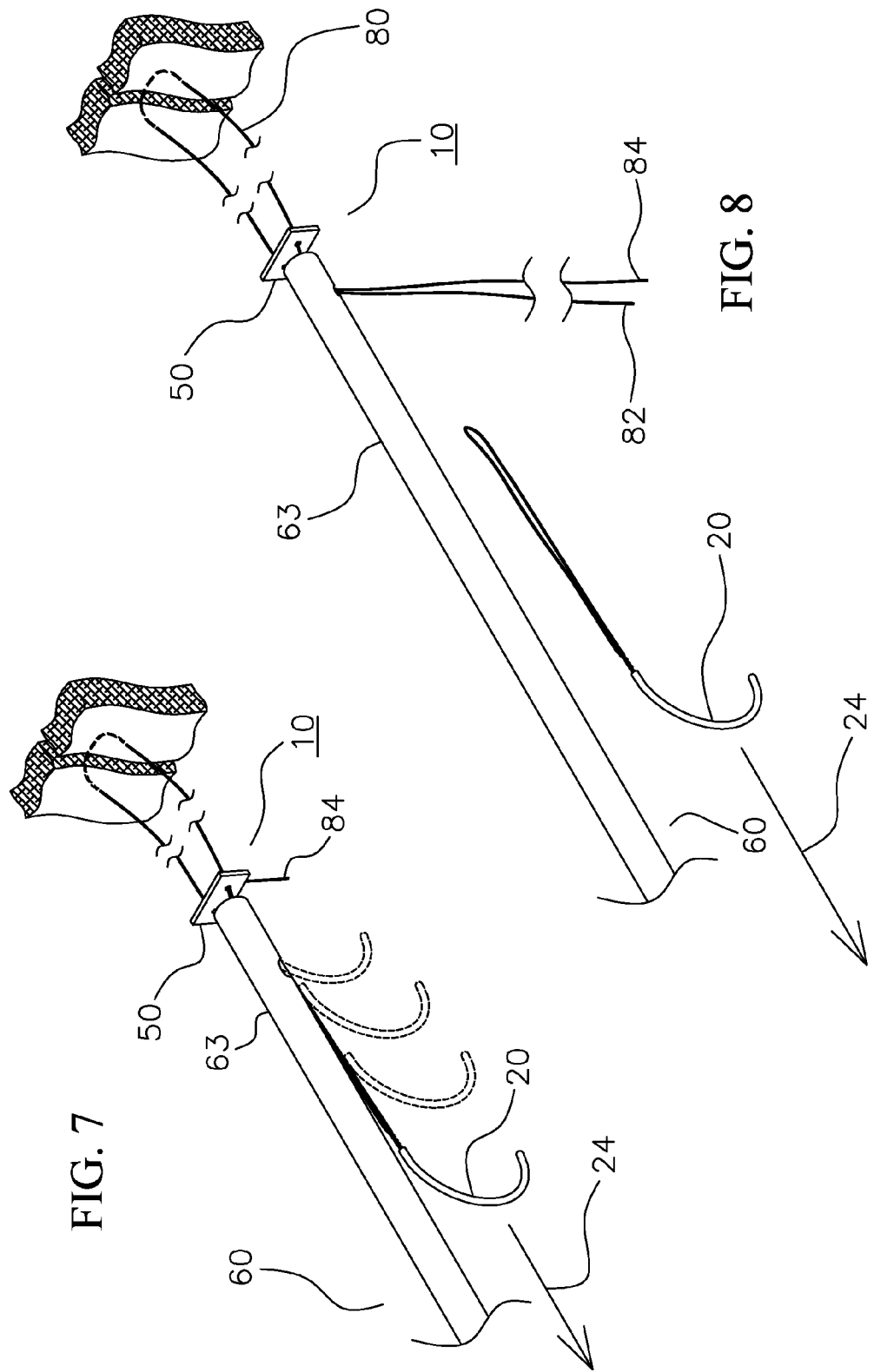

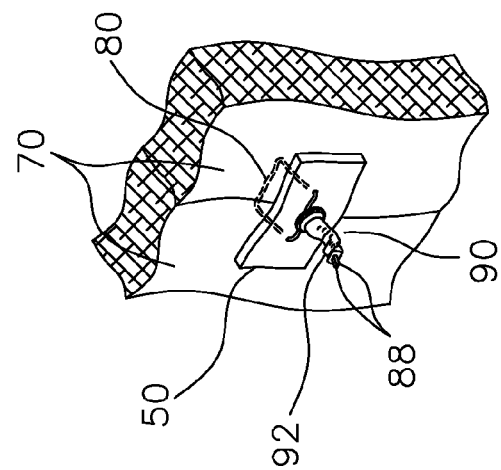
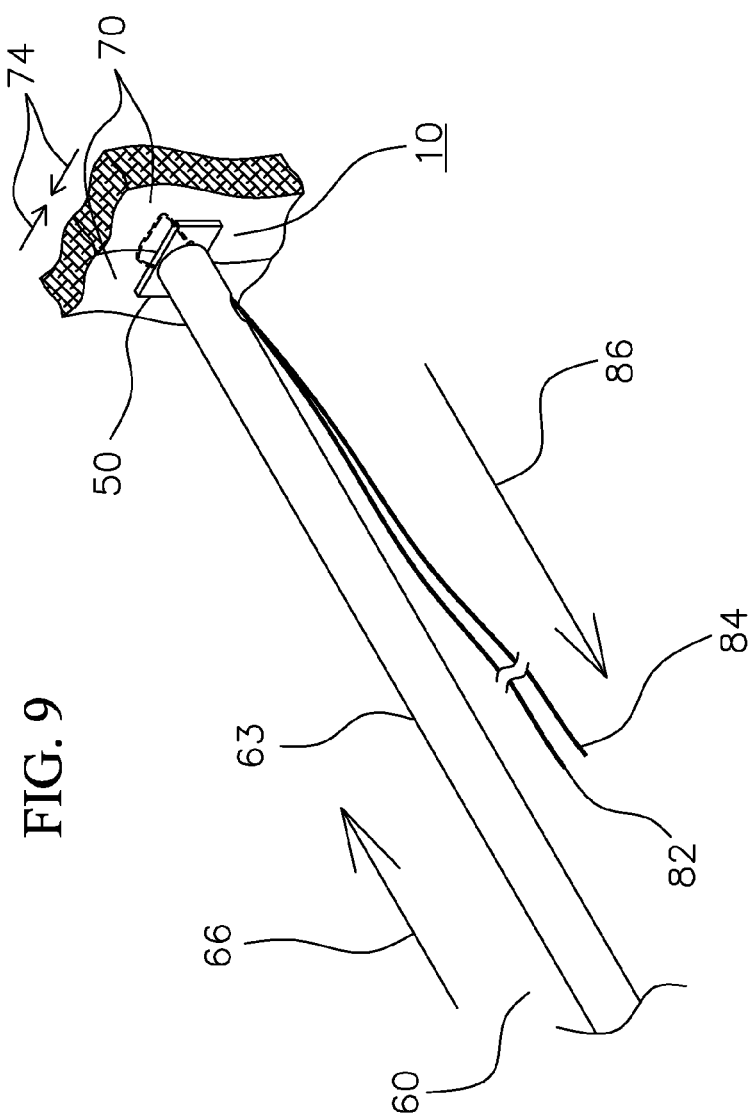

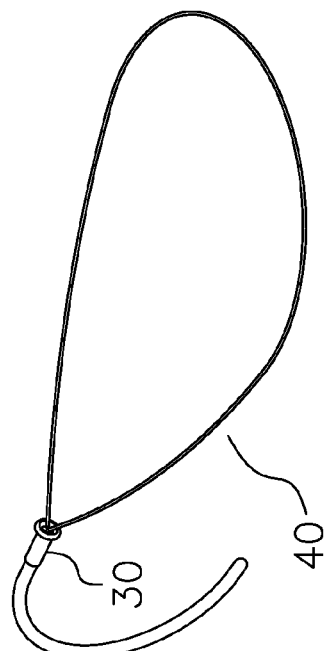
FIG. 12
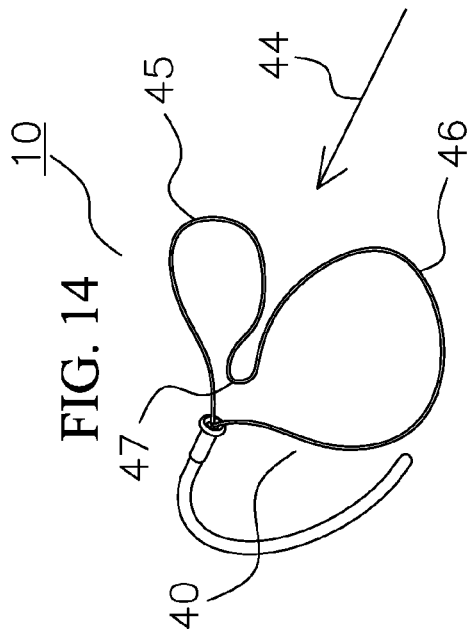
FIG. 14
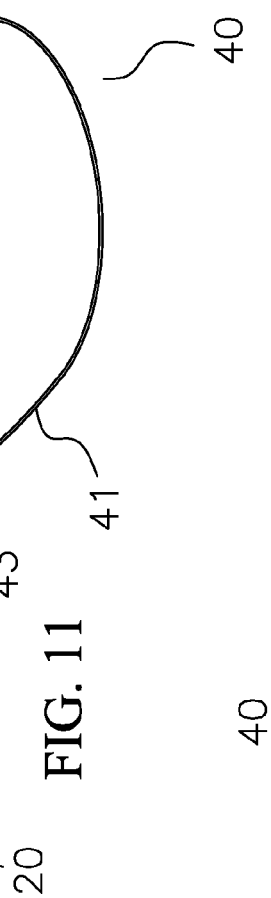
FIG. 11
FIG. 13

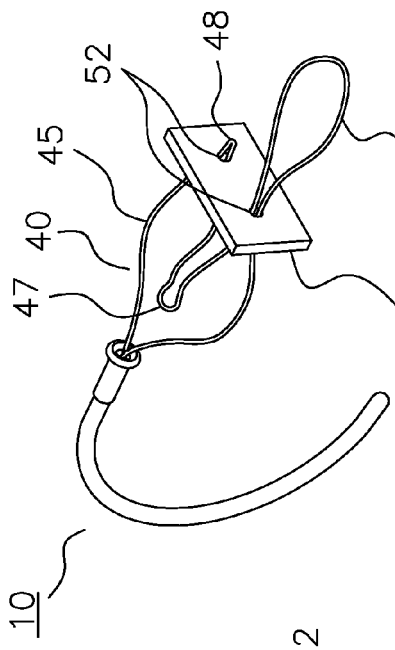
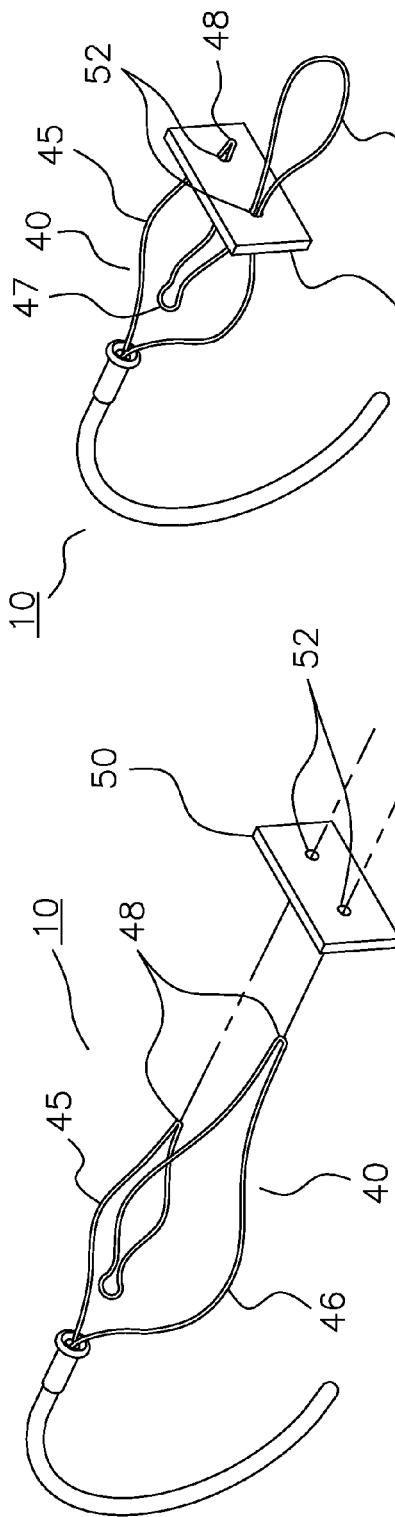
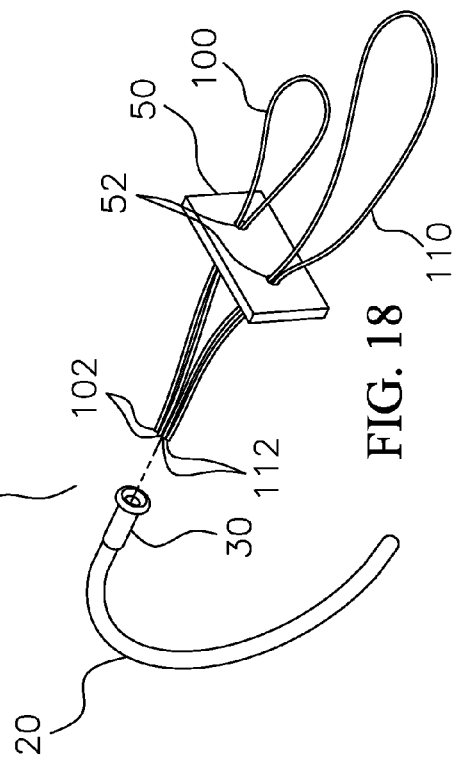
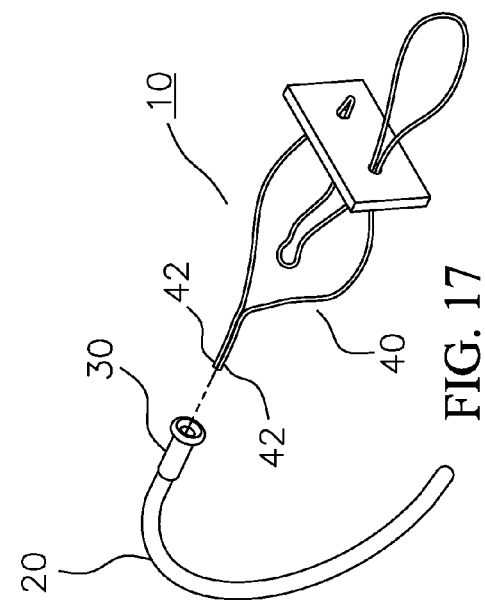

METHOD OF PASSING SUTURE TAILS THROUGH A SURGICAL PLEDGET

CROSS-REFERENCE TO RELATED APPLICATIONS

This application is a continuation of co-pending U.S. patent application Ser. No. 13/100,606, filed May 4, 2011, and entitled "MULTIPLE LOOP DEVICE FOR PASSING SUTURE TAILS THROUGH A SURGICAL PLEDGET". Accordingly, priority is hereby claimed to the May 4, 2011 filing date of this earlier patent application.

BACKGROUND OF THE INVENTION

This invention relates generally to surgical suturing and more particularly to a device for remotely placing a surgical pledget at a suturing site and drawing suture tails through the pledget to be secured proximally of the pledget.

DESCRIPTION OF RELATED ART

The general medical definition of a pledget is a small compress, tuft, or flat mass usually made of gauze or absorbent cotton that is laid over a wound or into a cavity to apply medication, exclude air, retain dressings or absorb discharged matter. The pledget concept, in a more specifically surgical application, often applies to material or bolster used to help reduce the risk of suture pulling through tissue that it is holding by cushioning and spreading the load of the suture against the underlying tissue. Surgical pledgets have been used throughout history and remain a routinely utilized adjunct to suture mediated tissue repair even in the most advanced modern surgical procedures.

In addition to pledgets distributing the retaining force of the suture over a larger area of tissue, they can aid in minimizing the leakage of bodily fluids, such as blood, that results from penetration of bodily tissue by a suture needle and suture. Pledgets may be left implanted permanently at a wound closure site or a prosthetic attachment site. If indicated, they can also be subsequently removed along with the sutures from the patient.

A pledget may be placed completely under a section of suture or it can be configured so that the suture passes through one or more sections of the substance or the body of the pledget itself. A pledget also may be placed before or after the suture has been passed through tissue. By passing the suture through the pledget, the suture and the pledget can be more conveniently and securely handled during the suture placement process. While a pledget could be placed under the suture and above the tissue without the suture traversing through the pledget, this is often not practical or reliable under certain surgical conditions, especially those involving the remote suturing as are needed in many minimally invasive surgical procedures.

Furthermore, a pledget not threaded with a suture is more readily dislodged during manipulation or by movement or change of shape (e.g., swelling resolution) of the tissue.

Pledget Description. Pledgets are usually small pieces of thin, relatively soft material intended to atraumatically distribute the suture compressional forces over a broad area. They are conventionally formed from biocompatible flexible materials such as foam, felt or fabric. Pledgets are often made from non-resorbable polyurethane, polyamide, polyethylene, polypropylene, polyethylene terephthalate, polytetrafluoroethylene (PTFE or Teflon®), or various absorbable polymers, such as polyglycolic acid or even pieces of autologous tissue. These materials are selected based on surgical judgment to offer sufficiently enhanced structural integrity to assure that after the suture is tied, the pledget is held securely but gently against the tissue surrounding the suture to prevent tearing of the suture through the tissue and to reduce or prevent bleeding at suture puncture wounds. Common pledgets are conventionally formed from flat cloth-like material and are usually configured in circular, oval or rectangular shapes. Pledgets can be supplied as loose individual pieces with or without preformed suture holes extending through full thickness of the pledget, with preformed specialized suture entrance slits to accommodate alternative methods of placement with suture as described for example in U.S. Pat. No. 4,823,794 or as sets of multiple connected pledgets as described, for example, in U.S. Pat. No. 5,733,308) or pre-loaded on sutures with needles (e.g., Gore-Tex TH-22 {Flagstaff, Ariz.} or Covidien 3336-51 {Mansfield, Mass.}). Pledgets not preloaded on suture are also commercially available (e.g., Ethicon PCP20 {Somerville, N.J.}, TFE Polymer Pledgets (Firm)) with or without pre-formed holes through the body of the pledget just large enough to accommodate a suture of the desired size.

Suturing with Pledgets. Pledgets are usually used when more than one tissue bite is performed with one suture. A single loop suture, called a simple interrupted suture, does not typically require a pledget since a single loop going through two edges of a wound would have only a pledget on top of the wound. When more than one tissue bite is required, it is more practical to use pledgets under the sections of suture not passing through the tissue. For example, a so-called double armed suture with a needle at each end and with a pledget on the suture between the needles can be used to provide a pledget located on top of the tissue between the tissue entrance holes of the needles at the side opposite from where the knot will be placed (Reed and Cortez, "Measured Tricuspid Annuloplasty: A Rapid and Reproducible Technique", Annals of Thoracic Surgery, Vol. 21, February, 1976, pp. 168-169.) After the needles have exited the tissue site, by passing these two needles through a second pledget, this second pledget is located on the knot side of the closure on the top of the tissue between the needle exit sites. For conventional hand-tied knots, both needles would typically then be cut off from the suture and the hand-tied knotting process would commence over the second pledget near the needles exit site. Tightening the suture draws the two pledgets together and holds the tissue in compression.

Alternative Suturing and Knotting Techniques. Alternative techniques of suture placement, especially those used with mechanically assisted suturing devices, often provide two suture ends left untied on one side of the wound closure site or a prosthetic attachment site (U.S. Pat. Nos. 6,997,931; 7,731,727; U.S. application Ser. No. 12/835,464). For automated mechanical knots, it would further be helpful to not only pass the suture through the pledget but to continue to pass the same suture ends through the mechanical knot. The use of a single loop wire snare to pull suture ends through a mechanical knot (U.S. Pat. Nos. 5,520,702; 5,643,289; 5,669,917; 6,368,334; 6,641,592; 7,235,086) is currently commercially available through the Titanium Knot® Quick Load® unit and the Cor-Knot™ Quick Load® unit for the TK and CK device products, respectively, from our company, LSI SOLUTIONS®, Victor, N.Y. This single loop suture snare approach is easily and quickly learned by surgeons; it has been successfully employed to help secure suture in thousands of patients throughout this country.

The use of pledgets with surgical suturing confers many compelling advantages, but placement of a pledget on the suture ends at the knot side of the suture still presents inconvenient challenges and unnecessary risks. A pledget preloaded onto a suture, either through the use of needles or passing suture ends through pre-placed holes in the pledget, provides more definitive capture of the pledget.

Prior to this invention, the requisite use of needles to pass suture through pledgets would require several extra steps, increase the risk of needle injury and infection, and may not prove possible in many modern surgical interventions. While reducing the risk to the surgical team of unnecessary needle exposure is critical, the advantages of pledgets for the patient should not be sacrificed because of the difficulties of hand threading the suture through the pledgets. Hand threading suture ends through tiny holes in pledgets is not practical and may not even be achievable in the diminished ambient light conditions of many video intensive operating rooms. Custom slotted pledgets can offer some benefits, but may not satisfy the requirements for ease-of-use, effectiveness and safety in minimally invasive surgery applications, especially those involving automated suturing or automated knot placement technologies. The currently marketed single loop wire snare devices now available for pulling suture through mechanical knots do not aid in the placement of suture through pledgets. Devices to reduce the dexterity requirements and complexity of modern surgical operations can decrease anesthesia and surgery durations and potentially improve patient outcomes. A surgeon should have the option for the expedited use of enhancements, like pledgets, based on clinical needs without concerns regarding reliability or excessive time expenditures. The present invention addresses these needs.

BRIEF SUMMARY OF THE INVENTION

Briefly stated and in accordance with an embodiment of the invention, surgical pledget assembly includes a pledget body having first and second apertures extending through the body, one or more snares passing through the apertures in the pledget body and including first and second suture engaging loops disposed on a distal side of the pledget, an optional third folding loop disposed on a proximal side of the pledget, and a handle secured to the ends of the snare or snares proximal to the pledget.

In accordance with another embodiment of the invention, a suturing sleeve is disposed on the snare between the handle and the proximal side of the pledget.

In accordance with yet another aspect of the invention, the handle comprises a hollow sleeve.

In accordance with another aspect of the invention, the handle is crimped to the ends of the snare.

In accordance with yet another aspect of the invention, the snare ends are twisted together.

In accordance with still another aspect of the invention, the handle is curved to make it easier to grasp.

In accordance with a further aspect of the invention, the snare includes suture engaging loops of different sizes.

In accordance with a still further aspect of the invention, the suturing sleeve includes an enlarged head and a crimpable body.

In accordance with another aspect of the invention, a method for drawing first and second suture tails through first and second apertures of a surgical pledget includes the steps of providing a surgical pledget having first and second apertures formed therein or a snare or snares formed into first and second suture engaging loops disposed distally of a pledget and an optional folding loop where the snare is a single piece, and first and second snare ends disposed proximally of a pledget; and passing the first and second suture tails through the first and second suture engaging loops respectfully; and then drawing the snare and the suture tails proximally through the pledget apertures by pulling the snare ends proximally until the snare is released from the pledget and the suture tails pass through the pledget apertures.

In accordance with another aspect of the invention, the method includes the step of securing the suture tails together on the proximal side of the pledget to close a wound for example.

In accordance with yet another aspect of the invention, securing the suture tails includes the step of securing the tails with a crimpable sleeve.

In accordance with yet another aspect of the invention, the method includes the step of passing the snare ends through a suture securing sleeve before drawing the snare ends and the suture tails proximally through the pledget and drawing the suture tails through the sleeve.

In accordance with a favored embodiment of the invention, the suture tails are crimped in the suture securing sleeve.

BRIEF DESCRIPTION OF THE SEVERAL VIEWS OF THE DRAWING(S)

While the novel aspects of the invention will be described with particularity in the appended claims, the invention itself together with further objects and advantages thereof may be more readily understood by reference to the following detailed description of the number presently preferred embodiments of the invention taken in conjunction with the accompanying drawings in which:

FIG. 1 is a distally oriented perspective view of a surgical pledget assembly in accordance with this invention as presented for use;

FIG. 2 is a proximally oriented perspective view of the pledget assembly of FIG. 1 as presented for use;

FIG. 5 is a proximal perspective view of the pledget assembly accepting suture tails from a wound site;

FIG. 6 is a proximal perspective view of the pledget assembly of FIG. 5 illustrating the initial passing of suture through the device;

FIG. 7 is a proximal perspective view of the pledget assembly of FIG. 6 illustrating the final stage of progression of the suture through the device;

FIG. 8 is a proximal perspective view of the pledget assembly of FIG. 7 demonstrating the suture completely passed through the device;

FIG. 9 is a proximal perspective view of the pledget assembly of FIG. 8 pressed against the wound site and closing the wound area via the tension of the suture;

FIG. 10 is a perspective view of the closed wound with applied suture securing sleeve;

FIG. 11 is an exploded perspective view detailing a representative sequential step in the assembly of the pledget assembly of this invention;

FIG. 12 is a perspective view of the pledget assembly disclosed in FIG. 11;

FIG. 13 is a perspective view illustrating the initialization of the forming process for the pledget assembly of FIG. 12;

FIG. 14 is a perspective view of the formed pledget assembly of FIG. 13;

FIG. 15 is an exploded perspective view of an additionally formed and adapted pledget assembly of FIG. 14;

FIG. 16 is a perspective view illustrating partial assembly of the pledget assembly illustrated in FIG. 15;

FIG. 17 is a perspective view of an embodiment of a pledget assembly in accordance with this invention illustrating a variation of the installed ends of the wire snare;

FIG. 18 is a perspective view of an embodiment of a pledget assembly in accordance with this invention wherein two separate wire snare loops are passed individually through a pledget.

DETAILED DESCRIPTION OF THE INVENTION

Figure 4:
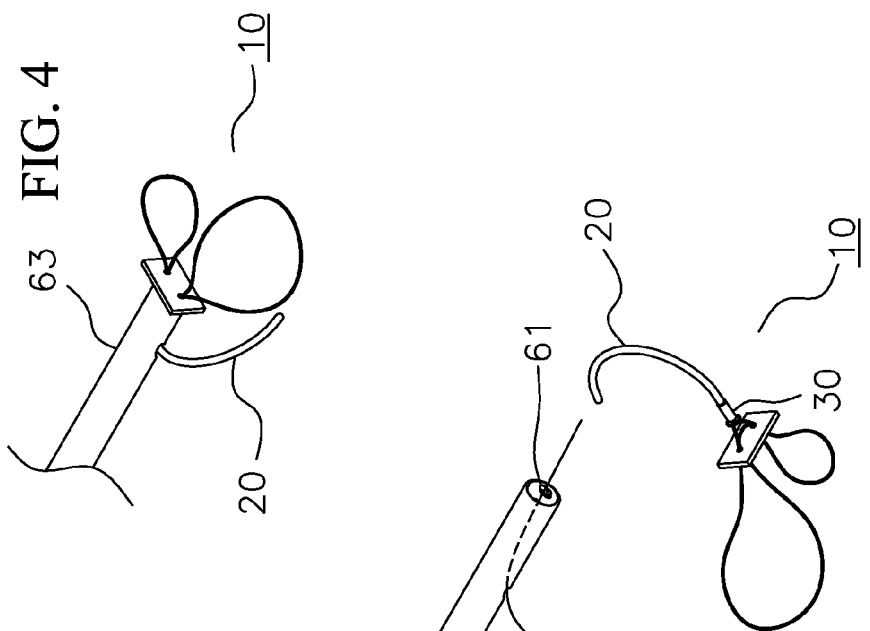
FIG. 4 is a perspective view of the distal end of the pledget assembly and corresponding application instrument presented in FIG. 3 as applied to its intended field of use.

Referring to FIGS. 1 and 2, a presently preferred embodiment of the invention is disclosed.

FIG. 1 shows a distal view of a dual snare pledget assembly 10 as presented for use. A large loop 46 and a small loop 45 having passed through and expanded outside of suture holes 52 formed in a pledget 50 in a fashion that allows for the positioning of the pledget 50 in proximity to a suture securing sleeve 30. While FIGS. 1-17 illustrate embodiments of the invention in which the large and small loops are formed from a single length of material, the loops may be formed separately as shown in FIG. 18.

FIG. 2 shows a proximal perspective view of the dual snare pledget assembly 10 of FIG. 1 relative to its intended field of use with the pledget 50 in position close to a head 32 of the suture securing sleeve 30. A folding loop 47 of a wire snare 40 transits the two suture holes 52 of the pledget 50.

Figure 3:
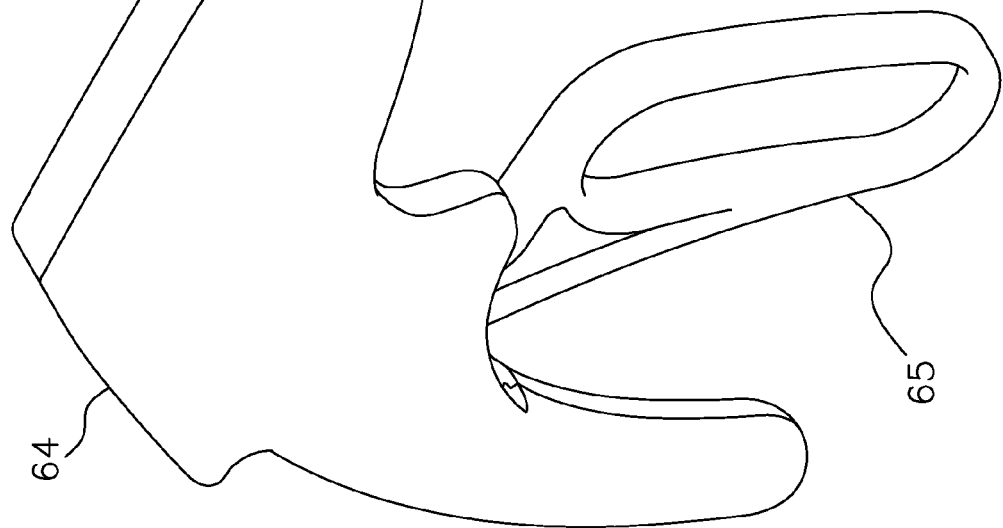
FIG. 3 is a perspective view of the pledget assembly presented in FIG. 1 in preparation for use in a corresponding application instrument when applied to its field of use.

FIG. 3 is a perspective view of the dual snare pledget assembly 10 with its preferred method of application in a mechanical crimping device 60. The mechanical crimping device 60 is preferably a commercially available product such as the TK Ti-Knot® Device™, or CK Cor-Knot™ Device™ which are marketed exclusively by LSI SOLUTIONS®, Inc. The curved handle 20 of the dual snare pledget assembly 10 is inserted into a sleeve receptacle 61 along an insertion path 62 located at the distal end of a barrel 63 that is fixedly attached to a handle 64 of the mechanical crimping device 60. The mechanical crimping device 60 is mechanically activated via a lever 65 which induces a physically crushing force onto the suture securing sleeve 30 leaving it permanently attached to suture tails emanating from a wound closure site.

Focusing on FIG. 4, the dual snare pledget assembly 10 is shown fully installed and securely seated in the barrel 63 of the mechanical crimping device 60 of FIG. 3. The curved handle 20 is passed through and protruding from the barrel 63. While a curved handle geometry is preferred to facilitate threading of the handle through the distal end of the mechanical crimping device and to provide greater purchase for pulling on the handle to operate the device during a procedure, a straight handle may also be used, preferably provided with a textured gripping surface.

FIGS. 5 through 8 illustrate the sequential threading, passing, and pulling of suture 80 through the dual snare pledget assembly 10, suture securing sleeve 30 and barrel 63 of the mechanical crimping device 60.

FIG. 5 depicts opposing sections of tissue 70 with emplaced suture 80. The suture 80 protrudes from sections of tissue 70 through suture exits 72 such that a left suture tail 82 and a right suture tail 84 remain separated from each other. The left suture tail 82 and the right suture tail 84 are directed towards the mechanical crimping device 60 of FIG. 3 and the installed dual snare pledget assembly 10 with the small loop 45 and large loop 46, respectively. Illustrated is the initial step wherein the left suture tail 82 is threaded through the small loop 45 and kept separated and untangled from the right suture tail 84 which is threaded through the large loop 46. It should be noted, however, that placement of a particular suture tail in a particular loop is not critical so long as the suture 80 is kept untangled, and only one suture tail is fed into each loop.

FIG. 6 shows the sequence of events after FIG. 5 wherein the curved handle 20 is extracted by hand from the barrel 63 of the mechanical crimping device 60 by pulling it in the direction 24. The small loop 45 and large loop 46 are drawn through the suture holes 52 in the pledget 50 and begin the process of passing the left suture tail 82 and right suture tail 84 through the mechanical crimping device 60.

FIG. 7 depicts the sequence of events after FIG. 6 wherein the curved handle 20 is extracted by hand further from the barrel 63 of the mechanical crimping device 60 in the pull direction 24. The previously passed small loop 45 and its threaded left suture tail 82, which are no longer visible, are almost pulled entirely through the barrel 63 and the large loop 46, which is no longer visible, and its threaded right suture tail 84 have passed through the pledget 50 and are being passed through the barrel 63. While small and large loops are preferred to reduce the bulk of the snare as it passes through the mechanical crimping device, loops of the same size may also be used.

FIG. 8 illustrates the final sequence of pulling suture 80 through the pledget 50 and out of the barrel 63 of the mechanical crimping device 60. The curved handle 20 is fully extricated from the barrel 63 in pull direction 24 which subsequently allows for the exit of the left suture tail 82 and the right suture tail 84 from the barrel 63.

Referring now to FIG. 9, the barrel 63 of the mechanical crimping device 60 is moved along engaging direction 66 and the left suture tail 82 and the right suture tail 84 are pulled taut in direction 86 such that the pledget 50 is cinched against the tissue 70, drawing the opposing sides towards each other in direction 74. Tension is maintained and the mechanical crimping device 60 is actuated to secure the suture with the crimped sleeve 90 (not shown in this view). While use of a sleeve to secure the suture is preferred, the suture may also be tied in conventional fashion.

FIG. 10 illustrates the effect of the actuated mechanical crimping device 60 as shown in FIG. 9 wherein the pledget 50 is snug to the tissue 70, the suture 80 is taut, and a crimped sleeve 90 is secured against the pledget 50 with trimmed suture 88 exiting a crimped barrel 92.

Referring to FIGS. 11 and 12, process steps are shown for a typical assembly of a pledget assembly in accordance with one aspect of the invention.

FIG. 11 shows a pledget assembly 10 preferably including a wire or fiber snare 40, a suture securing sleeve 30 having an enlarged head 32, and a curved handle 20. The wire snare 40 is formed of a biocompatible flexible wire such as 304 stainless steel or the like, or a natural or synthetic fiber such as silk or polypropylene or the like, into a loop 41 whose free ends 42 are secured together as a twisted pair end 43. The twisted pair end 43 of wire snare 40 is inserted through a bore 36 of suture securing sleeve 30 such that the head 32 is adjacent to the loop 41.

Traditionally, the suture securing sleeve 30 is made of a medical grade permanently implantable radiopaque material; such as titanium, although absorbable materials such as magnesium can be used. Suitable suture securing sleeves 30 are exclusively marketed by LSI SOLUTIONS®, Inc, and can be found under commercial trade names Ti-Knot® and Cor-Knot™ The twisted pair end 43 is inserted into a snare receptacle bore 22 of a curved handle 20 and permanently secured by mechanically crimping the handle. While twisting the ends of the wire snare 40 is preferred, the untwisted ends may, if desired, simply be inserted through the sleeve 30 into the handle 20 and crimped. Typical materials used in the forming of the curved handle 20 include fully hardened stainless steels in the 400 series regime.

FIG. 12 illustrates the assembled dual snare pledget assembly 10 of FIG. 11 before the single snare is formed into two loops. The wire snare 40 passes through the suture securing sleeve 30 and fixedly attached to the curved handle 20.

FIGS. 13 through 16 illustrate the forming sequence of the wire snare 40 in accordance with an embodiment of the invention.

FIG. 13 depicts the dual snare pledget assembly 10 in its raw form with the loop 41 being deformed in a folding direction 44 such that the presentation of a dual loop becomes evident.

FIG. 14 shows a dual snare pledget assembly 10 that having been formed in folding direction 44 creates a folding loop 47 and two disparate loops of wire; a small loop 45 and a large loop 46.

FIG. 15 demonstrates the additional forming of the wire snare 40 into formed points 48 to facilitate installation through suture holes 52 of the pledget 50. The large loop 46 and the small loop 45 are mechanically pinched to temporarily create formed points 48.

Referring to FIG. 16, the large loop 46 of the wire snare 40 has been passed through one of the suture holes 52 of the pledget 50 and expanded. The small loop 45 with its formed point 48 is shown inserted through and protruding from the opposing suture hole 52 of pledget 50.

FIG. 17 shows an embodiment of the invention in which the ends 42 of the wire snare 40 are not twisted or otherwise combined, but fed individually through the suture securing sleeve 30 and into the curved handle 20 where they are mechanically secured, for example, by crimping.

FIG. 18 shows an embodiment of the invention wherein free ends 102 of an individual small wire loop 100 and free ends 112 of a large wire loop 110 are separately fed through the suture holes 52 of pledget 50 and subsequently through the suture securing sleeve 30 and into the curved handle 20 where they are mechanically secured.

While the invention has been described in connection with certain presently preferred embodiments thereof, those skilled in the art will recognize that many modifications and changes may be made therein without departing from the broad scope of the invention which accordingly is intended to be defined solely by the appended claims.

The invention claimed is:

1. A method of drawing first and second suture tails through first and second apertures of a surgical pledget comprising:
   a) providing
      1) a surgical pledget having first and second apertures therein; and
      2) a snare passing through the pledget including:
         i) first and second suture engaging loops disposed on a distal side of the pledget; and
         ii) a handle secured to ends of the first and second suture engaging loops on a proximal side of the pledget;
   b) passing the first and second suture tails through the first and second suture engaging loops respectively; and
   c) drawing the suture tails proximally through the pledget apertures by pulling the handle proximally until the snare is released from the pledget and the suture tails pass through the pledget apertures.

2. The method of claim 1, further comprising:
securing the first and second suture tails together on the proximal side of the pledget.

3. The method of claim 2, wherein securing the first and second suture tails together on the proximal side of the pledget comprises securing the first and second suture tails together on the proximal side of the pledget with a securing sleeve.

4. The method of claim 1, further comprising drawing the suture tails proximally through a securing sleeve by pulling the handle.

5. The method of claim 4 further comprising crimping the securing sleeve.

6. The method of claim 1, wherein the first and second suture engaging loops are formed from a single length of material and the snare further comprises a folding loop on the proximal side of the pledget.

7. A method of passing suture through a pledget, comprising:
passing one or more first suture tails through a first suture engaging loop extending out of a first aperture in the pledget on a distal side of the pledget;
passing one or more second suture tails through a second suture engaging loop extending out of a second aperture in the pledget on the distal side of the pledget; and
drawing the one or more first and second suture tails proximally through their respective pledget apertures by pulling a handle coupled to the first and second suture engaging loops on a proximal side of the pledget.

8. The method of claim 7, further comprising:
securing at least one of the one or more first and second suture tails on the proximal side of the pledget.

9. The method of claim 7, further comprising:
securing at least one of the one or more first suture tails together with at least one of the one or more second suture tails on the proximal side of the pledget.

10. The method of claim 7, further comprising:
securing at least one of the one or more first suture tails to at least one of the one or more second suture tails with a securing sleeve.

11. The method of claim 7, further comprising drawing the one or more first suture tails and the one or more second suture tails through a securing sleeve on the proximal side of the pledget.

12. The method of claim 11, further comprising crimping the securing sleeve.

13. The method of claim 7, wherein the first and second suture engaging loops are formed from a single length of material.

14. A method of passing suture through a pledget, comprising:
passing a first suture tail through a first suture engaging loop extending out of a first aperture in the pledget on a distal side of the pledget;
passing a second suture tail through a second suture engaging loop extending out of a second aperture in the pledget on the distal side of the pledget; and drawing the first and second suture tails proximally through their respective pledget apertures by pulling a handle coupled to the first and second suture engaging loops on a proximal side of the pledget.

15. The method of claim 14, further comprising:
securing at least one of the first and second suture tails on the proximal side of the pledget.

16. The method of claim 14, further comprising:
securing the first and second suture tails together on the proximal side of the pledget.

17. The method of claim 16, wherein the first and second suture tails are secured together with a securing sleeve.

18. The method of claim 14, further comprising drawing the first and second suture tails through a securing sleeve on the proximal side of the pledget.

19. The method of claim 18, further comprising crimping the securing sleeve.

20. The method of claim 14, wherein the first and second suture engaging loops are formed from a single length of material.

\* \* \* \* \*